(12) United States Patent
Hokazono et al.

(10) Patent No.: US 7,572,617 B2
(45) Date of Patent: Aug. 11, 2009

(54) **THERMOSTABLE RIBONUCLEASE H OBTAINED FROM *ARCHEOGLOBUS PROFUNDUS***

(75) Inventors: Shigekazu Hokazono, Otsu (JP); Takashi Uemori, Otsu (JP); Tetsuki Tanaka, Moriyama (JP); Ikunoshin Kato, Koka-gun (JP)

(73) Assignee: Takara Bio Inc., Shiga (JP)

( * ) Notice: Subject to any disclaimer, the term of this patent is extended or adjusted under 35 U.S.C. 154(b) by 369 days.

(21) Appl. No.: 10/526,073

(22) PCT Filed: Aug. 26, 2003

(86) PCT No.: PCT/JP03/10727

§ 371 (c)(1),
(2), (4) Date: Feb. 28, 2005

(87) PCT Pub. No.: WO2004/020621

PCT Pub. Date: Mar. 11, 2004

(65) Prior Publication Data

US 2007/0037247 A1 Feb. 15, 2007

(30) Foreign Application Priority Data

Aug. 30, 2002 (JP) .............................. 2002-254153

(51) Int. Cl.
*C07K 14/00* (2006.01)
*C12N 9/16* (2006.01)
*C12Q 1/14* (2006.01)
*C12N 15/00* (2006.01)
*C12N 5/10* (2006.01)
*C12N 1/21* (2006.01)
*C12P 21/00* (2006.01)
*C07H 21/00* (2006.01)

(52) U.S. Cl. ................. 435/196; 435/320.1; 435/252.3; 435/325; 435/69.1; 435/19; 530/350; 536/23.2

(58) Field of Classification Search .................. 435/196, 435/320.1, 69.1, 252.3, 325, 19; 530/350; 536/23.2
See application file for complete search history.

(56) References Cited

U.S. PATENT DOCUMENTS 5,268,289 A 12/1993 Dahl et al.
5,610,066 A 3/1997 Fuller et al.

FOREIGN PATENT DOCUMENTS

| EP | 1 318 197 A1 | 6/2003 |
| JP | 2533671 B2 | 6/1996 |
| JP | 11-32772 A | 2/1999 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Klenk et al., PIR accession No. E69327, 1997.*
Current Protocols in Molecular Biology, Hybridization Analysis of DNA Blots, pp. 2.10.8-2.10.11, 1993.*
Chapados, et al, "Structural Biochemistry of a Type 2 RNase H: RNA primer recognition and removal during DNA replication", J. Mol. Biol., 307:541-556. (2001).
Itaya, Mitsuhiro and Kanae Kondo, "Molecular cloning of a ribonuclease H (RNase HI) gene from an extreme thermophile *Thermus thermophilus* HB8: a thermostable RNase H can functionally replace the *Escherichia coli* enzyme in vivo", Nucleic Acids Research, 19(16):4443-4449. (1991).
Kanaya, et al, "Overproduction and preliminary crytstallographic study of ribonuclease H from *Escherichia coli*", Journal of Biological Chemistry, 264(20):11546-11549. (1989).
Lopez-Garcia, et al, "Plasmid pGS5 from the Hyperthermophilic Achaeon *Archaeoglobus profundus* is negatively supercoiled", Journal of Bacteriology, 182(17):4998-5000. (Sep. 2000).

* cited by examiner

*Primary Examiner*—Delia M Ramirez
(74) *Attorney, Agent, or Firm*—Browdy and Neimark, P.L.L.C.

(57) ABSTRACT

An isolated polypeptide having a thermostable ribonuclease H activity from *Archaeoglobus profundus* is highly useful in genetic engineering, as well as a gene encoding this polypeptide and a genetic engineering process for producing the polypeptide.

2 Claims, 1 Drawing Sheet

THERMOSTABLE RIBONUCLEASE H OBTAINED FROM *ARCHEOGLOBUS PROFUNDUS*

TECHNICAL FIELD

The present invention relates to a polypeptide, specifically a polypeptide having a ribonuclease H activity which is highly valuable for genetic engineering. The present invention also relates to a gene that is useful for producing said polypeptide by genetic engineering. The present invention further relates to a method for producing said polypeptide by genetic engineering.

BACKGROUND ART

There are endo-type and exo-type ribonucleases (RNA-degrading enzymes). Their substrate specificities are diverse, and they are involved in complicated physiological activities. Enzymes such as ribonuclease $T_1$, ribonuclease $T_2$, ribonuclease H, ribonuclease P, ribonuclease I, ribonuclease II, ribonuclease III, ribonuclease IV, ribonuclease L are known to have ribonuclease activities.

Ribonuclease H (hereinafter also referred to as RNase H) was first isolated from calf thymus by W. H. Stein and P. Hausen in 1969. RNase Hs are currently classified into cellular RNase Hs and viral RNase Hs. The cellular RNase Hs are widely present in eukaryotes such as various animal cells and yeasts and prokaryotes such as *Escherichia coli*, whereas the viral RNase Hs are present in RNA tumor viruses. Several kinds of RNase H activities are present in a cell. They require divalent metal ions such as $Mg^{2+}$ and $Mn^{2+}$.

An RNase H from *Escherichia coli* is a hydrolase that consists of 155 amino acids, has a molecular weight of about 17 kDa and has a substrate specificity of specifically cleaving only the RNA strand in a DNA-RNA hybrid in an endo-type manner. The resulting oligomer has a phosphate group at the 5' end and a hydroxyl group at the 3' end.

RNase HI and RNase HII have been identified as RNase Hs from *E. coli*. It has been shown that RNase HI has the following physiological functions in the replication of the Col E1 plasmid: 1) it degrades RNAs bound to portions other than the normal replication origin to ensure the normal replication origin; and 2) it synthesizes an RNA primer specific for the normal replication origin. On the other hand, the function of RNase HII remains unknown.

RNase Hs have uses as exemplified below based on the substrate specificities, and attention is paid to RNase Hs as very valuable enzymes:

1) removal of template mRNA upon cDNA cloning;
2) removal of poly(A) region in mRNA; and
3) fragmentation of RNA.

It is considered that RNase H increasingly becomes important with the development of genetic engineering. However, the expression level of this enzyme in *E. coli* is quite low. Then, production of this enzyme. using recombinant DNA techniques has been attempted. RNase Hs produced using recombinant DNA techniques are now supplied from BRL, Amersham Pharmacia Biotech, Takara Bio and the like.

These commercially available recombinant RNase Hs are produced using *Escherichia coli* as a host (Kanaya et al., The Journal of Biological Chemistry, 264:11546-11549 (1989)). A method of producing an RNase H from a thermophile, which is much more stable than RNase H from *E. coli*, using *E. coli* has been reported (Kanaya et al., Dai 2 Kai Nippon Tanpakukougakukai Nenkai Program/Abstract (1990) pp. 69; Japanese Patent No. 2533671). However, the enzymatic activity of the RNase H from a thermophile produced using *E. coli* was lower than that of RNase H from *E. coli*.

As described above, only thermostable RNase Hs whose productivities and enzymatic activities are lower than those of RNase H from *E. coli* are available. Thus, development of a thermostable RNase H whose productivity and enzymatic activity are equivalent to or more than those of the RNase H from *E. coli* has been desired for expanding the uses of RNase H.

Then, RNase Hs having varying thermostabilities have been cloned in order to solve the above-mentioned problems. Examples thereof include RNase Hs derived from *Bacillus caldotenax, Pyrococcus furiosus, Thermotoga maritima, Archaeoglobus fulgidus, Thermococcus litoralis, Thermococcus celer* and *Pyrococcus horikoshii* as described in WO 02/22831.

Further examples. include RNase Hs derived from *Thermus thermophilus* (Nucleic Acids Research, Vol. 19, No. 16, p 4443-4449 (1991); U.S. Pat. No. 5,268,289), *Pyrococcus furiosus* (U.S. Pat. No. 5,610,066), *Pyrococcus* sp. KOD1 (JP-A 11-32772) and *Archaeoglobus fulgidus* (Journal of Molecular Biology, Vol. 307, p 541-556 (2001)).

However, there have been many problems to be improved concerning these RNase Hs such as low thermostability, decreased activity on a. DNA-RNA hybrid having short RNA strand and low specific activity. Then, development of further thermostable RNase H having distinct substrate specificity or mode of action has been desired to meet the importance of RNase H which is considered to be increased more and more with the development of genetic engineering.

DISCLOSURE OF INVENTION

The main object of the present invention is to provide a polypeptide having an RNase H activity which is highly valuable for genetic engineering, a gene encoding. said polypeptide and a method for producing said polypeptide by genetic engineering.

In view of the circumstances as described above, the present inventors have studied intensively and conducted screening in order to obtain a thermostable RNase H. As a result, the present inventors have found a thermostable RNase H polypeptide having a high RNase H activity. Furthermore, the present inventors have found that the productivity of the thus obtained thermostable RNase H in production using genetic engineering techniques. is high. Thus, the present invention has been completed.

The present invention is outlines as follows. The first aspect of the present invention relates to a polypeptide having a thermostable ribonuclease H activity,. selected from the group consisting of:

(a) a polypeptide having the amino acid sequence of SEQ ID NO:1;

(b) a polypeptide having an amino acid sequence in which at least one amino acid residue is deleted, added, inserted or substituted in the amino acid sequence of SEQ ID NO:1; and (c) a polypeptide having an amino acid sequence that shares at least 54% homology with the amino acid sequence of SEQ ID NO:1.

The second aspect of the present invention relates to a nucleic acid encoding a polypeptide having a thermostable ribonuclease H activity, selected from the group consisting of:

(a) a nucleic acid encoding a polypeptide having the amino acid sequence of SEQ ID NO:1;

(b) a nucleic acid encoding a polypeptide having an amino acid sequence in which at least one amino acid residue is deleted, added, inserted or substituted in the amino acid sequence of SEQ ID NO:1;

(c) a nucleic acid encoding a polypeptide having an amino acid sequence that shares at least 54% homology with the amino acid sequence of SEQ ID NO:1;

(d) a nucleic acid having the nucleotide sequence of SEQ ID NO:2;

(e) a nucleic acid consisting of a nucleotide sequence in which at least one nucleotide is deleted, added, inserted or substituted in the nucleotide sequence of SEQ ID NO:2 such that the deletion, addition, insertion or substitution of the nucleotide results in translation into an amino acid sequence;

(f) a nucleic acid capable of hybridizing to any one of the nucleic acids of (a) to (d) or complementary strands thereof under stringent conditions; and (g) a nucleic acid having a nucleotide sequence that shares at least 61% homology with the nucleotide sequence of SEQ ID NO:2.

The third aspect of the present invention relates to a recombinant DNA comprising the nucleic acid of the second aspect.

The fourth aspect of the present invention relates a transformant transformed with the recombinant DNA of the third aspect.

The fifth aspect of the present invention relates to a method for producing a polypeptide having a thermostable ribonuclease H activity, the method comprising:

culturing the transformant of the fourth aspect; and collecting a polypeptide having a thermostable ribonuclease H activity from the culture.

The sixth aspect of the present invention relates a polypeptide having a thermostable ribonuclease H activity, obtainable by culturing a transformant into which a plasmid pApr108 is transferred. An *Escherichia coli* strain harboring this plasmid is deposited under Budapest Treaty on Aug. 20, 2002 (date of original deposit) under accession number FERM BP-8433 at International Patent Organism Depositary, National Institute of Advanced Industrial Science and Technology, AIST Tsukuba Central 6, 1-1, Higashi 1-chome, Tsukuba-shi, Ibaraki 305-8566, Japan.

BEST MODE FOR CARRYING OUT THE INVENTION

Figure 1:
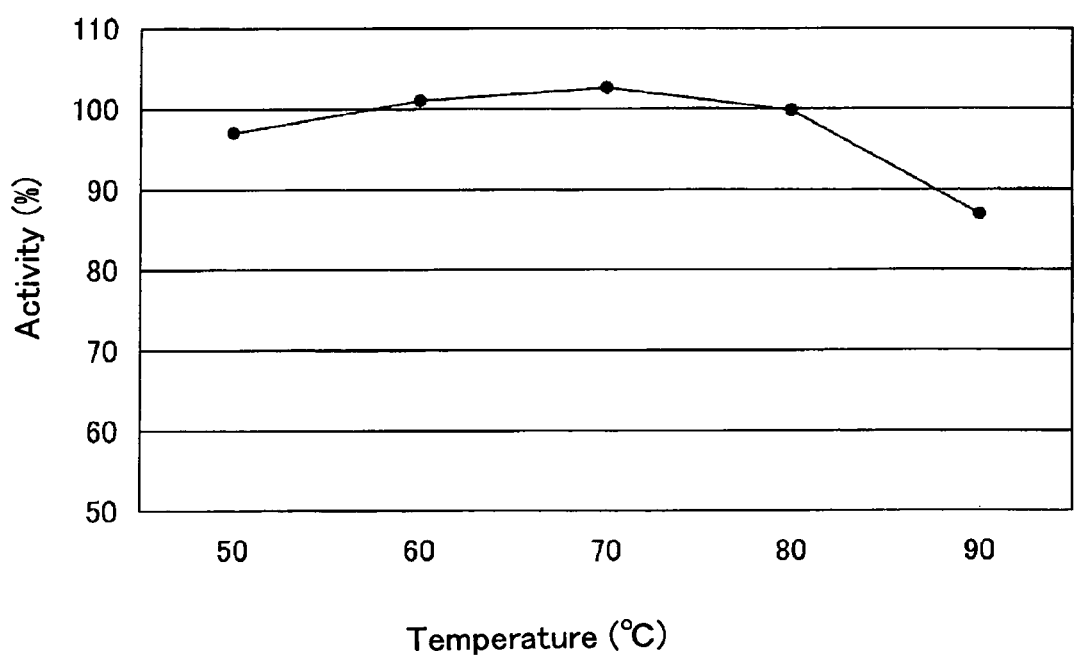
FIG. 1 illustrates the thermostability of the RNase H of the present invention.

Hereinafter, the present invention will be described in detail.

As used herein, an RNase H refers to a hydrolase that has a substrate specificity of specifically cleaving only the RNA strand in a DNA-RNA hybrid in an endo-type manner, wherein the oligomer resulting from the cleavage has a phosphate group at the 5' end and a hydroxyl group at the 3' end.

Although it is not intended to limit the present invention, having a thermostable RNase H activity as used herein with respect to a polypeptide means that the polypeptide has an RNase H activity after incubating it at a temperature of 70° C. or above for 15 minutes.

For example, a thermostable RNase H activity can be determined as follows.

1 mg of poly(rA) or poly(dT) (both from Amersham Pharmacia Biotech) is dissolved in 1 ml of 40 mM tris-HCl (pH 7.7) containing 1 mM EDTA to prepare a poly(rA), solution and a poly(dT) solution.

The poly(rA) solution (to a final concentration of 20 μg/ml) and the poly(dT) solution (to a final concentration of 30 μg/ml) are then added to 40 mM tris-HCl (pH 7.7) containing 4 mM $MgCl_2$, 1 mM DTT, 0.003% BSA and 4%. glycerol. The mixture is reacted at 37° C. for 10 minutes and then cooled to 4° C. at prepare a poly(rA)-poly(dT) solution.

1 μl of an enzyme solution is added to 100 μl of the poly (rA)-poly(dT) solution. The mixture is reacted at 40° C. for 10 minutes. 10 μl of 0.5 M EDTA is added thereto to terminate the reaction. Absorbance at 260 nm is then measured. As a control, 10 μl of 0.5 M EDTA is added to the reaction mixture, the resulting mixture is reacted at 40° C. for 10 minutes, and the absorbance is then measured. A value (difference in absorbance) is determined by subtracting the absorbance for the control from the absorbance for the reaction in the absence of EDTA. Thus, the concentration of nucleotide released from poly(rA)-poly(dT) hybrid by the enzymatic reaction is determined on the basis of the difference in absorbance. Thus, the thermostable RNase H activity according to the present invention can be determined.

Alternatively, the thermostable RNase H activity according to the present invention can be determined as follows. 100 μl of a reaction mixture [20 mM HEPES-potassium hydroxide (pH 8.5), 0.01% bovine serum albumin (Takara Bio), 1% dimethyl sulfoxide, 4 mM magnesium acetate, 20 μg/ml poly(dT) (Amersham Pharmacia Biotech), 30 μg/ml poly(rA) (Amersham Pharmacia Biotech)] which has been incubated at 40° C. is added to 1 μl of an enzyme solution whose activity is to be determined. The mixture is reacted at 40° C. for 10 minutes. The reaction is then terminated by adding 10 μl of 0.5 M EDTA (pH 8.0). Absorbance at 260 nm is then measured.

One unit of RNase H is defined as an amount of enzyme that increases $A_{260}$ corresponding to release of 1 nmol of ribonucleotide in 10 minutes which can be calculated according to the following equation:

$$\text{Unit} = [\text{Difference in Absorbance} \times \text{Reaction Volume (ml)}]/0.0152$$

The polypeptide of the present invention is exemplified by a polypeptide having the amino acid sequence. of SEQ ID NO:1. The present invention also encompasses a polypeptide having an amino acid sequence in which at least one amino acid residue is deleted, added, inserted or substituted in the amino acid sequence of SEQ ID NO:1 as long as it exhibits a thermostable RNase H activity.

A mutation such as deletion, insertion, addition or substitution of an amino acid in an amino acid sequence may be generated in a naturally occurring polypeptide. Such mutation may be generated due to a polymorphism or a mutation of the DNA encoding the polypeptide, or due to a modification of the polypeptide in vivo or during purification after synthesis. However, it is known that such a mutated polypeptide may exhibit a physiological or biological activity substantially equivalent to that of a polypeptide without a mutation if such a mutation is present in a portion that is not important for the retention of the activity or the structure of the polypeptide.

This is applicable to a polypeptide in which such a mutation is artificially introduced into an amino acid sequence of a polypeptide. In this case, it is possible to generate more various mutations. For example, it is known that a polypeptide in which a cysteine residue in the amino acid sequence of human interleukin-2 (IL-2) is replaced by a serine retains the interleukin-2 activity (Science, 224:1431 (1984)).

Furthermore, it is known that certain polypeptides have peptide regions that are not indispensable to their activities. Such peptide regions are exemplified by a signal peptide in a polypeptide to be secreted extracellularly, or a prosequence or pre-prosequence found in a precursor of a protease. Most of such regions are removed after translation or upon conversion into an active polypeptide. Such a polypeptide has a primary structure different from that of a polypeptide without the region to be removed, but finally exhibits an equivalent function.

A gene having the nucleotide sequence of SEQ ID NO:2 which is isolated according to the present invention encodes a polypeptide having the amino acid sequence of SEQ ID NO:1. This polypeptide has a thermostable RNase H activity. The polypeptide of the present invention includes a polypeptide from which a peptide region that is not indispensable to its activity has been deleted therefrom.

When a polypeptide is produced by genetic engineering, a peptide chain that is irrelevant to the activity of the polypeptide of interest may be added at the amino terminus or the carboxyl terminus of the polypeptide. For example, a fusion polypeptide, in which a portion of an amino terminus region of a polypeptide that is expressed at a high level in the host to be used is added at the amino terminus of the polypeptide of interest, may be prepared in order to increase the expression level of the polypeptide of interest. In another case, a peptide having an affinity for a specific substance may be added at the amino terminus or the carboxyl terminus of the polypeptide of interest in order to facilitate the purification of the expressed polypeptide. The added peptide may remain added if it does not have a harmful influence on the activity of the polypeptide of interest. If necessary, it may be engineered such that it can be removed from the polypeptide of interest by appropriate treatment, for example, by limited digestion with a protease.

Thus, a polypeptide having an amino acid sequence in which at least one amino acid residue is deleted, inserted, added or substituted in the amino acid sequence of SEQ ID NO:1 disclosed herein is encompassed by the present invention if it has a thermostable RNase H activity.

Furthermore, a polypeptide having an amino acid sequence that shares at least 54%, preferably 60%, more preferably 70%, most preferably 85% homology with the amino acid sequence of SEQ ID NO:1 disclosed herein is encompassed by the present invention if it has a thermostable RNase H activity.

The homology can be determined using, for example, a computer program DNASIS-Mac (Takara Bio), a computer algorithm FASTA (version 3.0; Pearson, W. R. et al., Pro. Natl. Acad. Sci., 85:2444-2448, 1988) or a computer algorithm BLAST (version 2.0, Altschul et al., Nucleic Acids Res. 25:3389-3402, 1997).

For example, a polypeptide having an amino acid sequence that shares at least 54% homology with the amino acid sequence of the ribonuclease H from *Archaeoglobus profundus* (SEQ ID NO:1) is encompassed by the present invention if it has a thermostable RNase H activity.

The polypeptide of the present invention can be produced, for example, by (1) purification from a culture of a microorganism producing the polypeptide of the present invention, or (2) purification from a culture of a transformant containing a nucleic acid encoding the polypeptide of the present invention.

(1) Purification from Culture of Microorganism Producing the Polypeptide of the Present Invention The microorganism producing the polypeptide of the present invention is exemplified by *Archaeoglobus profundus* (DSM5631) which can be purchased from Deutsche Sammlung von Mikroorganismen und Zellkulturen GmbH. The microorganism is cultured under conditions suitable for the growth of the microorganism. Preferably, culture conditions that increase the expression level of the polypeptide of interest are used. The polypeptide of interest produced in the cells or the culture medium can be purified according to a method conventionally used for purifying a protein.

A method conventionally used for culturing a thermostable bacterium can be utilized for the cultivation of the above-mentioned strain. Nutrients that can be utilized by the strain are added to the culture medium. For example, starch can be used as a carbon source, and Tryptone, peptone and yeast extract can be used as nitrogen sources. A metal salt such as a magnesium salt, a sodium salt or an iron salt may be added to a culture medium as a trace element. In addition, it may be advantageous to use artificial seawater for the preparation of a culture medium in case of a thermostable marine bacterium, for example.

The culture may be a standing culture or a spinner culture. For example, a dialysis culture method as described in Applied and Environmental Microbiology, 55:2086-2088 (1992) may be used. It is preferable to determine the culture conditions and the cultivation time depending on the strain or the composition of the culture medium to be used such that the productivity of the polypeptide becomes maximum.

A cell-free extract is first prepared in order to obtain a polypeptide. The cell-free extract can be prepared, for example, by collecting cells from a culture by centrifugation, filtration or the like and then disrupting the cells. A cell disruption method highly effective for extracting the enzyme of interest may be selected from sonication, disruption using beads, treatment with a lytic enzyme and the like. If the polypeptide is secreted into a culture supernatant, the polypeptide in the culture supernatant is concentrated by ammonium sulfate precipitation, ultrafiltration or the like. The concentrated polypeptide is used as a cell-free extract. A method conventionally used for purifying a protein can be used to isolate the polypeptide from the thus obtained cell-free extract. For example, ammonium sulfate precipitation, ion exchange chromatography, hydrophobic chromatography, gel filtration chromatography and the like can be used in combination.

(2) Purification from Culture of Transformant Transformed with Recombinant DNA containing Nucleic Acid Encoding the Polypeptide of the Present Invention The polypeptide of the present invention can be obtained from a transformant transformed with a recombinant DNA that contains a nucleic acid encoding the polypeptide of the present invention, for example, a nucleic acid having a nucleotide sequence of SEQ ID NO:2. A polypeptide having an amino acid sequence of SEQ ID NO:1 is produced using a nucleic acid having a nucleotide sequence of SEQ ID NO:2.

The polypeptide of the present invention may be purified from a culture obtained by culturing a transformant into which the plasmid of the present invention, pApr108, is transferred.

There is no specific limitation concerning the host to be transformed. Examples thereof include those conventionally used in the field of recombinant DNA such as *Escherichia* coli, *Bacillus subtilis*, yeast, filamentous fungi, plants, animals, cultured plant cells and cultured animal cells.

For example, the polypeptide of the present invention can be obtained by culturing *Escherichia coli* harboring a plasmid in which the nucleic acid of the present invention is linked downstream from a lac promoter or a T7 phage promoter under conventional. culture conditions, for example, in LB medium (10 g/l Tryptone, 5g/l yeast extract, 5 g/l NaCl, pH 7.2) containing 100 µg/ml of ampicillin at 37° C. until logarithmic growth phase, adding isopropyl-β-D-thiogalactopyranoside at a final concentration of 1 mM thereto and further culturing at 37° C. to express the polypeptide in the cultured cells.

Cells are collected by centrifugation after cultivation, disrupted by sonication, and a supernatant collected by centrifugation is used as a cell-free extract. This cell-free extract exhibits a thermostable RNase H activity. The polypeptide of the present invention can be purified from the cell-free extract by using known methods such as ion exchange chromatography, gel filtration, hydrophobic chromatography and ammonium sulfate precipitation. Naturally, a partially purified product obtained during the purification process as described above also exhibits an RNase H activity. Since the polypeptide of the present invention expressed in *Escherichia coli* harboring a plasmid linked to the nucleic acid of the present invention is thermostable, it may be purified as follows. For example, the cultured cell and/or the cell-free extract is heated at a temperature of 40° C. or above for about 10 minutes, and heat-denatured insoluble proteins derived from the host is removed. An optimal temperature or time may be suitably selected for the heat treatment.

As described above, when the polypeptide of the present invention is expressed at normal temperature (e.g., 37° C.) using a transformant harboring a nucleic acid encoding the polypeptide, the resulting expression product retains the activity, the thermostability and the like. That is, the polypeptide of the present invention can assume its inherent higher-order structure even if it is expressed at a temperature quite different from the growth temperature of the original producer cell.

The nucleic acid of the present invention is a nucleic acid that encodes the polypeptide of the present invention. Specifically, it is (1) a nucleic acid that encodes a polypeptide having the amino acid sequence of SEQ ID NO:1, or an amino acid sequence in which at least one amino acid residue is deleted, added, inserted or substituted in the sequence and having a thermostable RNase H activity; (2) a nucleic acid having the nucleotide sequence of SEQ ID NO:2; (3) a nucleic acid that has a nucleotide sequence that is capable of hybridizing to the nucleic acid of (1) or (2) above under. stringent conditions, or that shares at least 61%, preferably 70%, more preferably 80%, most preferably 90% homology with the nucleotide sequence of (1) or (2) above, and that encodes a polypeptide having a thermostable RNase H activity, or the like.

The homology of the nucleotide sequence can be determined using a computer program DNASIS-Mac, or a computer algorithm FASTA (version 3.0) or BLAST (version 2.0).

As used herein, a nucleic acid means a single-stranded or double-stranded DNA or RNA. If the nucleic acid of (2) above is an RNA, it is represented by a nucleotide sequence in which T is replaced by U in the nucleotide sequence of SEQ ID NO:2, for example.

For example, the nucleic acid of the present invention can be obtained as follows.

The nucleic acid of (2) above having the nucleotide sequence of SEQ ID NO:2 can be isolated as follows. A genomic DNA is prepared according to a conventional method from *Archaeoglobus profundus* (DSM5631) cultured as described above for the polypeptide of the present invention. The genomic DNA is used to construct a DNA library. The nucleic acid can be isolated from the DNA library. Also, the nucleic acid can be obtained by amplifying a nucleic acid having a nucleotide sequence of SEQ ID NO:2 by a polymerase chain reaction (PCR) using the genomic DNA as a template.

Furthermore, a nucleic acid encoding a polypeptide having a thermostable RNase H activity similar to that of the polypeptide of the present invention can be obtained on the basis of the nucleotide sequence of the nucleic acid encoding the polypeptide of the present invention provided by the present invention (e.g., the nucleotide sequence of SEQ ID NO:2). Specifically, a DNA encoding a polypeptide having a thermostable RNase H activity can be screened, using the nucleic acid encoding the polypeptide of the present invention or a portion of the nucleotide sequence as a probe for hybridization, from a DNA extracted from cells, PCR products obtained using the DNA as a template or the like. Alternatively, a DNA encoding a polypeptide having a thermostable RNase H activity can be amplified using a gene amplification method such as a PCR using a primer designed based on the above-mentioned nucleotide sequence. Additionally, a DNA encoding a polypeptide having a thermostable RNase H activity can be chemically synthesized. The nucleic acids of (1) or (3) above can be obtained according to such a method.

A nucleic acid fragment containing only a portion of the nucleic acid of interest may be obtained according to the above-mentioned method. In this case, the entire nucleic acid of interest can be obtained as follows. The nucleotide sequence of the obtained nucleic acid fragment is determined to confirm that the fragment is a portion of the nucleic acid of interest. Hybridization is carried out using the nucleic acid fragment or a portion thereof as a probe. Alternatively, a PCR is carried out using a primer synthesized on the basis of the nucleotide sequence of the nucleic acid fragment.

"Hybridizing under stringent conditions" means that a nucleic acid is capable of hybridizing under conditions as described in T. Maniatis et al. (eds.), Molecular Cloning: A Laboratory Manual 2nd ed., Cold Spring Harbor Laboratory (1989) or the like. For example, it refers to capability of hybridization under the following conditions. A membrane onto which a nucleic acid is immobilized is incubated with a probe in 6×SSC (1×SSC: 0.15 M NaCl, 0.015 M sodium citrate, pH 7.0) containing 0.5% SDS, 0.1% bovine serum albumin (BSA), 0.1% polyvinylpyrrolidone, 0.1% Ficoll 400 and 0.01% denatured salmon sperm nucleic acid at 50° C. for 12 to 20 hours. After incubation, the membrane is washed in 2×SSC containing 0.5% SDS at 37° C. while changing the SSC concentration down to 0.1× and the temperature up to 50° C. until the signal from the immobilized nucleic acid can be distinguished from background, and the probe is then detected. The activity of the protein encoded by the thus obtained novel nucleic acid is determined as described above, thereby confirming whether or not the nucleic acid is the nucleic acid of interest.

If an oligonucleotide probe is to be used, "stringent conditions" refer to, for example, incubation at a temperature of [Tm−25° C.] overnight in a solution containing 6×SSC, 0.5% SDS, 5×Denhardt's and 0.01% denatured salmon sperm nucleic acid although it is not intended to limit the present invention.

Tm of an oligonucleotide probe or primer can be determined, for example, according to the following equation:

$$Tm=81.5-16.6(\log_{10}[Na^+])+0.41(\% \, G+C)-(600/N)$$

wherein N is the chain length of the oligonucleotide probe or primer; % G+C is the content of guanine and cytosine residues in the oligonucleotide probe or primer.

If the chain length of the oligonucleotide probe or primer is shorter than 18 bases, Tm can be estimated, for example, as the sum of the product of the number of A+T (adenine and thymine) residues multiplied by 2(° C.) and the product of the number of G+C residues multiplied by 4(° C.):

$$[(A+T)\times 2+(G+C)\times 4]$$

According to the present invention, a nucleic acid that is capable of hybridizing to the nucleic acid encoding the polypeptide of the present invention under stringent conditions is encompassed by the present invention as long as it encodes a polypeptide having a thermostable RNase H activity even if it does not have the same nucleotide sequence as that disclosed herein, as described above.

It is known that one to six codon(s) (a combination of three bases), which defines an amino acid in a gene, is assigned for each amino acid. Thus, many nucleic acids can encode one specific amino acid sequence although it depends on the amino acid sequence. Nucleic acids are not necessarily stable in the nature. Generation of a mutation in a nucleotide sequence is not unusual. A mutation generated in a nucleic acid may not alter the encoded amino acid sequence (called a silent mutation). In this case, it can be said that a different nucleic acid encoding the same amino acid sequence is generated. Thus, one cannot deny the possibility that various nucleic acids encoding the same amino acid sequence can be generated in the course of passage of an organism containing an isolated nucleic acid encoding one specific amino acid sequence. Furthermore, it is not difficult to artificially produce various nucleic acids encoding the same amino acid sequence if one uses various genetic engineering techniques.

For example, if a codon used in an original nucleic acid encoding a protein of interest is one whose codon usage is low in the host to be used for producing the protein by genetic engineering, the expression level of the protein may be low. In this case, the codon is artificially converted into one frequently used in the host without altering the encoded amino acid sequence aiming at elevating the expression level of the protein of interest (e.g., JP-B 7-102146). It is needless to say that various nucleic acids encoding one specific amino acid sequence can be artificially prepared as described above. They may also be generated in the nature.

The nucleic acid encoding the polypeptide of the present invention (e.g., a nucleic acid having the nucleotide sequence of SEQ ID NO:2) can be ligated to an appropriate vector to construct a recombinant DNA. There is no specific limitation concerning the vector to be used for the construction of the recombinant DNA. For example, plasmid vectors, phage vectors and virus vectors can be used. A suitable vector for the object of the recombinant DNA is selected.

Furthermore, a transformant can be produced by transferring the recombinant DNA into an appropriate host. There is no specific limitation concerning the host to be used for the production of a transformant. Microorganisms such as bacteria, yeasts and filamentous fungi as well as cultured cells from animals, plants, insects and the like can be used. The polypeptide of the present invention can be produced in large quantities by culturing the transformant to produce the polypeptide of the present invention in the culture.

(3) Polypeptide of the Present Invention

The polypeptide of the present invention obtained as described above can be utilized for a nucleic acid amplification method, for example, as described in WO 00/56877 or WO 02/16639. RNase H activities of some of conventional RNase Hs may be reduced depending on the length of RNA portion in a chimeric nucleic acid (e.g., DNA-RNA-DNA). The polypeptide of the present invention is less susceptible to influence of the length of RNA portion. Thus, it can be preferably used for the base substitution detection method as described in WO 02/064833 or the cycling probe method as described in BioTechniques, Vol. 20, No. 2, p 240-248 (1996). Since the polypeptide of the. present invention has a property that its RNase H activity can be retained after treatment at 95° C. for 15 minutes, it can be used for a variety of uses.

EXAMPLES

The following Examples illustrate the present invention in more detail, but are not to be construed to limit the scope thereof.

Example 1

Cloning of *Archaeoglobus profundus* RNase H Gene (1) Preparation of Genomic DNA from *Archaeoglobus profundus*

Cells of *Archaeoglobus profundus* (purchased from Deutsche Sammlung von Mikroorganismen und Zellkulturen GmbH; DSM5631) collected from 10 ml of a culture were suspended in 100 μl of a mixture containing 20% sucrose and 50 mM tris-HCl (pH 8.0). 20 μl of 0.5 M EDTA and 10 μl of 10 mg/ml aqueous solution of lysozyme chloride (Nacalai Tesque) were added thereto. The mixture was reacted at 20° C. for 2 hours. After reaction, 800 μl of a mixture containing 150 mM NaCl, 1 mM EDTA and 20 mM tris-HCl (pH 8.0), 10 μl of 20 mg/ml proteinase K (Takara Bio) and 50 μl of 10% aqueous solution of sodium lauryl sulfate were added to the reaction mixture. The mixture was incubated at 37° C. for 1 hour. After reaction, the mixture was subjected to phenol-chloroform extraction, ethanol precipitation and air-drying. The precipitate was then dissolved in 50 μl of TE to obtain a genomic DNA solution.

(2) Cloning of Middle Portion of RNase H Gene

Oligonucleotides RN-F1 (SEQ ID NO:3) and RN-R2 (SEQ ID NO:4) were synthesized on the basis of portions conserved among amino acid sequences of various thermostable RNase Hs.

A PCR was carried out in a volume of 100 μl using 5 μl of the *Archaeoglobus profundus* genomic DNA solution prepared in Example 1-(1) as a template, and 100 pmol each of RN-F1 and RN-R2 as primers. TaKaRa Ex Taq (Takara Bio) was used as a DNA polymerase for the PCR according to the attached protocol. The PCR was carried out as follows: 50 cycles of 94° C. for 30 seconds, 45° C. for 30 seconds and 72° C. for 1 minute. After reaction, the reaction mixture was subjected to Microcon-100 (Takara Bio) for removal of primers and concentration of the reaction mixture to obtain an about 0.5-kb DNA fragment AprF1R2.

(3) Cloning of Upstream and Downstream Portions of RNase H Gene

The nucleotide sequence of the about 0.5-kb fragment AprF1R2 obtained in Example 1-(2) was determined. A specific oligonucleotide AprRN-1 (SEQ ID NO:5) for cloning the upstream portion and a specific oligonucleotide AprRN-2 (SEQ ID NO:6) for cloning the downstream portion were synthesized on the basis of the determined nucleotide sequence. In addition, 48 primers as shown in Table 1 were synthesized. The tag sequence in Table 1 is shown in SEQ NO:7.

TABLE 1

5'-tag sequence-NN-SSSSSSS-3'
(N: mixture of G, A, T and C; S represents the nucleotide sequence below)

| No. | Nucleotide sequence |
|---|---|
| 1 | ggagcag |
| 2 | ggcaaag |
| 3 | ggcaacg |
| 4 | ggcacag |
| 5 | ggcattg |
| 6 | ggccaag |
| 7 | ggccttg |
| 8 | ggctaag |
| 9 | ggctacg |
| 10 | ggctcag |
| 11 | ggctttg |
| 12 | gggacag |
| 13 | gggcaag |
| 14 | gggcttg |
| 15 | gggtacg |
| 16 | ggtaacg |
| 17 | ggtacgg |
| 18 | ggtagcg |
| 19 | gtaacgg |
| 20 | gtaagcg |
| 21 | gtacacg |
| 22 | gtagacg |
| 23 | gtagcgg |
| 24 | gtcaacg |
| 25 | gcaccag |
| 26 | gcagacg |
| 27 | gcagcag |
| 28 | gcatggg |
| 29 | gccaaag |
| 30 | gccacag |
| 31 | gccattg |
| 32 | gcccaag |
| 33 | gcccttg |
| 34 | gcctacg |
| 35 | gcctcag |
| 36 | gcctttg |
| 37 | gcgcaag |
| 38 | gcgcttg |
| 39 | gcggacg |
| 40 | gcgtaag |
| 41 | gctacgg |
| 42 | gctcacg |
| 43 | gctccag |
| 44 | gcttgcg |
| 45 | gcttggg |
| 46 | ggacacg |
| 47 | ggaccag |
| 48 | ggagacg |

PCRs were carried out in reaction mixtures containing 1 µl of the *Archaeoglobus profundus* genomic DNA solution prepared in Example 1-(1) as a template, a combination of 20 pmol of AprRN-1 or 20 pmol of AprRN-2 and 20 pmol of one of the 48 primers listed in Table 1, 20 mM tris-acetate (pH 8.5), 50 mM potassium acetate, 3 mM magnesium acetate, 0.01% BSA, 30 µM each of dNTPs and 2.5 units of TaKaRa Ex Taq DNA polymerase (Takara Bio). PCRs were carried out as follows: incubation at 94° C. for 3 minutes; and 40 cycles of 98° C. for 10 seconds, 50° C. for 10 seconds and 72° C. for 40 seconds. A portion of each PCR product was subjected to agarose gel electrophoresis. Microcon-100 (Takara Bio) was used to remove primers from reaction mixtures selected for the generation of single bands and to concentrate the reaction mixtures. The concentrates were subjected to direct sequencing to screen for fragments containing the upstream or downstream portion of the RNase H. As a result, it was shown that an about 600-bp PCR-amplified fragment Apr-1A5 contained the upstream portion of the RNase H gene and an about 500-bp PCR-amplified fragment Apr-2D9 contained the downstream portion.

(4) Cloning of Entire RNase H Gene

Primers AprNde (SEQ ID NO:8) and AprBam (SEQ ID NO:9) were synthesized on the basis of the nucleotide sequence.

A PCR was carried out in a volume of 100 µl using 1 µl of the *Archaeoglobus profundus* genomic DNA solution obtained in Example 1-(1) as a template, and 20 pmol each of AprNde and AprBam as primers. Ex Taq DNA polymerase (Takara Bio) was used as a DNA polymerase for the PCR according to the attached protocol. The PCR was carried out as follows: 40 cycles of 94° C. for 30 seconds, 55° C. for 30 seconds and 72° C. for 1 minute. An about 0.7-kb amplified DNA fragment was digested with NdeI and BamHI (both from Takara Bio). Then, plasmids pAPR111Nd and pApr108 were constructed by incorporating the resulting DNA fragment between NdeI and BamHI sites in a plasmid vector pTV119Nd (a plasmid in which the NcoI site in pTV119N is converted into a NdeI site) or pET3a (Novagen), respectively.

(5) Determination of Nucleotide Sequence of DNA Fragment containing RNase H Gene The nucleotide sequences of the DNA fragments. inserted into pAPR111Nd and pApr108 obtained in Example 1-(4) were determined according to a dideoxy method.

Analyses of the determined nucleotide sequences revealed the existence of an open reading frame presumed to encode RNase H. The nucleotide sequence of the open reading frame in pApr108 is shown in SEQ ID NO:2. The amino acid sequence of RNase H deduced from the nucleotide sequence is shown in SEQ ID NO:1. The PCR fragments AprF1R2, Apr-1A5 and Apr-2D9 correspond to a region from the 11th to 449th nucleotides in SEQ ID NO:2, a region from the 59th nucleotide toward the 5' end, and a region from the 373rd nucleotide toward the 3' end, respectively. *Escherichia coli* HMS174DE3 transformed with the plasmid pApr108 is designated and indicated as *Escherichia coli* HMS174/pApr108, and deposited on Aug. 20, 2002 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-8433. Analyses using a DNA sequence input analysis system DNASIS Ver. 3.6 (Takara Bio) revealed a protein of 24.4 kDa with an isoelectric point of 8.50. The protein was assumed to be classified into RNase HII based on nucleotide sequence comparisons.

(6) Expression of *Archaeoglobus profundus* RNase H Gene

*Escherichia coli* JM109 transformed with pAPR111Nd was inoculated into 10 ml of LB medium containing 100 µg/ml of ampicillin and 1 mM IPTG and cultured with shaking at 37° C. overnight. After cultivation, cells collected by centrifugation were suspended in 176.3 µl of a buffer (20 mM tris-HCl (pH 8.0), 1 mM EDTA) and sonicated. A supernatant obtained by centrifuging the sonicated suspension at 12,000 rpm for 10 minutes was heated at 70° C. for 10 minutes and then centrifuged again at 12,000 rpm for 10 minutes to collect a supernatant as a heated supernatant. Similarly, *Escherichia coli* HMS174(DE3) transformed with pApr108 was inoculated into 10 ml of LB medium containing 100 µg/ml of ampicillin and cultured with shaking at 37° C. overnight.

After cultivation, cells collected by centrifugation were processed according to the procedure as described above to obtain a heated supernatant of Apr RNase H.

The enzymatic activities were measured for the heated supernatants as follows.

1 mg of poly(rA) or poly(dT) (both from Amersham Pharmacia Biotech) was dissolved in 1 ml of 40 mM tris-HCl (pH 7.7) containing 1 mM EDTA to prepare a poly(rA) solution and a poly(dT) solution.

The poly(rA) solution (to a final concentration of 20 μg/ml) and the poly(dT) solution (to a final concentration of 30 μg/ml) were then added to 20 mM HEPES-KOH (pH 7.8) containing 4 mM $MgCl_2$, 0.1% DMSO and 0.01% BSA. The mixture was reacted at 40° C. for 10 minutes and then cooled to 4° C. to prepare a poly(rA)-poly(dT) solution.

1 μl of the heated supernatant of Apr RNase H was added to 100 μl of the poly(rA)-poly(dT) solution. The mixture was reacted at 40° C. for 10 minutes. 10 μl of 0.5 M EDTA was added thereto to terminate the reaction. Absorbance at 260 nm was then measured. As a control, 10 μl of 0.5 M EDTA was added to the reaction mixture, the resulting mixture was reacted at 40° C. for 10 minutes, and the absorbance was then measured. The absorbance for the control was subtracted from the absorbance for the reaction in the absence of EDTA to determine a value, difference in absorbance. The concentration of nucleotide released from poly(rA)-poly(dT) hybrid by the enzymatic reaction was determined on the basis of the difference in absorbance. One unit of RNase H was defined as an amount of enzyme that increases $A_{260}$ corresponding to release of 1 nmol of ribonucleotide in 10 minutes which was calculated according to the following equation. If a diluted enzyme solution was used, the value obtained using the equation was corrected based on the dilution rate:

Unit=[Difference in Absorbance×Reaction Volume (ml)]/0.0152

As a result, an RNase H activity was observed for the heated supernatant of Apr RNase H.

(7) Preparation of Purified RNase H Preparation

*Escherichia coli* BL21 (DE3) transformed with pApr108 obtained in Example 1-(4) was inoculated into 400 ml of LB medium containing 100 μg/ml of ampicillin and cultured with shaking at 37° C. for 17 hours. After cultivation, cells collected by centrifugation were suspended in 500 ml of Buffer A [20 mM tris-HCl (pH 8.0), 1 mM EDTA, 2 mM phenylmethanesulfonyl fluoride, 10 mM 2-mercaptoethanol] and sonicated. A supernatant obtained by centrifuging the sonicated suspension at 14,000 rpm for 30 minutes was heated at 70° C. for 15 minutes. It was then centrifuged again at 14,000 rpm for 30 minutes to collect a supernatant. Thus, 400 ml. of a heated supernatant was obtained.

The heated supernatant was subjected to DE52 anion exchange column (Whatman) equilibrated with Buffer A and washed with Buffer A. As a result, RNase H flowed through the DE52 column.

The protein solution flowed through the DE52 column was subjected to P-II cation exchange column (Whatman) equilibrated with Buffer B (20 mM tris-HCl (pH 7.0), 1 mM EDTA, 100 mM NaCl, 10 mM 2-mercaptoethanol) and eluted with a linear gradient of 100 mM to 1000 mM NaCl. As a result, an RNase H fraction eluted with about 500 mM NaCl was obtained.

150 ml of the RNase H fraction was concentrated to a volume of 50 ml using polyethyleneglycol (PEG) 20000. 150 mM of Buffer C (20 mM tris-HCl (pH 7.0), 1 mM EDTA, 10 mM 2-mercaptoethanol) was added to the concentrate, and the mixture was subjected to Heparin-Sepharose OL-6B heparin affinity column (Amersham BioSciences) equilibrated with Buffer B and eluted with a linear gradient of 100 mM to 500 mM NaCl. As a result, an RNase H fraction eluted with about 250 mM NaCl was obtained.

130 ml of the RNase H fraction was concentrated to a volume of 10 ml using PEG 20000. The concentrate was subjected to HiLoad 26/60 Superdex G200HR gel filtration column (Amersham BioSciences) equilibrated with Buffer D (20 mM tris-HCl (pH 7.0), 0.5 mM EDTA, 200 mM NaCl, 10 mM 2-mercaptoethanol) and eluted with Buffer D. As a result, 25 ml of an RNase H fraction was obtained.

35 ml of Buffer C was added to 25 ml of the RNase. H fraction, and the mixture was subjected to SP-Sepharose FF cation exchange column (Amersham BioSciences). equilibrated with Buffer B and eluted with a linear gradient of 100 mM to 500 mM NaCl. As a result, 50 ml of an RNase H fraction eluted with about 250 mM NaCl was obtained.

50 ml of the RNase H fraction was concentrated to a volume of 11 ml by centrifugation using Ultrafree-4 BIOMAX-5K (Millipore). 11 ml of the concentrate was dialyzed against Shape Buffer (25 mM tris-HCl (pH 7.0), 0.5 mM EDTA, 30 mM NaCl, 5 mM 2-mercaptoethanol, 50% glycerol), and 4.5 ml of an RNase H solution was obtained.

The thus obtained RNase H was used as Apr RNase H preparation.

The enzymatic activity of the Apr RNase H preparation was measured as described in Example 1-(6). As a result, an RNase H activity was observed for the Apr RNase H preparation.

Example 2

Homology Search

Homology searches were conducted for the amino acid sequence of RNase H from *Archaeoglobus profundus* (Apr) obtained in Example 1 and the nucleotide sequence encoding the same. Calculation of homology was conducted using a computer algorithm FASTA (version 3.2; Pearson, W. R. et al., Pro. Natl. Acad. Sci., 85:2444-2448, 1988) as a search program.

Gene database searches were conducted for Apr RNase H using the computer algorithm FASTA. As a result, the highest homologies between the amino acid and nucleotide sequences of Apr RNase H and those of one presumed to be of a ribonuclease were 53% and 60%, respectively.

Example 3

Examination of Thermostability of RNase H

Thermostability of *Archaeoglobus profundus* RNase H was examined using *Escherichia coli* transformed with pApr108 obtained in Example 1-(6). The *E. coli* strain was cultured, a crude enzyme extract prepared from the culture was heated at 95° C. for 15 minutes, and the RNase H activity was determined according to the method as described in Example 1-(6). As a result, an RNase H activity was observed for the RNase H derived from *Archaeoglobus profundus*.

In addition, Apr RNase H at a concentration of 5. units/ml in a heat treatment buffer (25 mM tris-HCl (pH 8.0), 5 mM mercaptoethanol, 30 mM NaCl, 0.5 mM EDTA, 0.1% BSA, 50% glycerol) was heated for 10 minutes at 50, 60, 70, 80 or 90° C., and the remaining activity was determined. The sample with or without heat treatment was added, at a final concentration of 0.2 units/ml, to an activity measurement solution (at final concentrations, 32 mM HEPES-potassium hydroxide buffer (pH 7.8), 100 mM potassium acetate, 1% DMSO, 0.05% BSA, 4 mM magnesium acetate, 0.2 µM substrate DNA-RNA-DNA and 1 µM templateW49 (SEQ ID NO:16)). The degradation rate per enzyme unit was determined with probeW3 (SEQ ID NO:15). The results are shown FIG. 1, defining the activity of RNase H without heat treatment as 100. Apr RNase H had almost 100% of the activity after heating at 50 to 80° C., and 86.9±7.0% remaining activity after reaction at 90° C. for 10 minutes.

Example 4

Examination of HBV Detection using ICAN System with Apr RNase H

A 560-bp PCR-amplified fragment corresponding to a part of HBV X protein gene (SEQ ID NO:10) was inserted into pT7Blue T vector by TA cloning. The resulting plasmid was used as an HBV positive control.

The composition of the reaction mixture was as follows: at final concentrations, 32 mM HEPES-potassium hydroxide buffer (pH 7.8), 100 mM potassium acetate, 1% DMSO, 0.01% BSA, 4 mM magnesium acetate, 600 µM each of dNTPs, 11 units of BcaBEST DNA polymerase, 50 pmol each of primers HBVF-2 (SEQ ID NO:11) and HBVR-1 (SEQ ID NO:12), $10^3$ copies of the HBV positive control, and 1.625, 3.25, 6.5 or 13 units of Apr RNase H (final volume of 25 µl). The reaction mixtures were placed in a thermal cycler which had been set at 55° C. and incubated for 60 minutes.

After reaction, 3 µl each of the reaction mixtures was subjected to electrophoresis on 3.0% agarose gel. As a result, the 76-bp amplification products of interest were observed using the respective amounts of RNase H.

The sensitivity for the HBV positive control was examined by carrying out similar experiments using $10^2$ copies, 10 copies or 1 copy of the HBV positive control. As a result, when 6.5 units of Apr RNase H were added, the highest sensitivity was observed and 1 copy of the HBV positive control could be detected.

Next, RNase HII from *Pyrococcus furiosus* (Pfu RNase HII), RNase HII from *Archaeoglobus fulgidus* (Afu RNase HII) and RNase HII from *Thermococcus litoralis* (Tli RNase HII) were prepared as described in WO 02/22831. They were used for detection of HBV using the above-mentioned ICAN system and the sensitivities were compared with that observed with Apr RNase H. When Pfu RNase HII was used, the highest sensitivity was observed using 2.2 units of the added enzyme with sensitivity of 10 copies of the HBV positive control. When Afu RNase HII was used, the highest sensitivity was observed using 2.2 units of the added enzyme with sensitivity of 10 copies of the HBV positive control. When Tli RNase HII was used, the highest sensitivity was observed using 8 units of the added enzyme with sensitivity of 10 copies of the HBV positive control.

As described above, one copy of the HBV positive control could be detected using Apr RNase H for detection of the HBV gene using the ICAN system. Thus, it was confirmed that the highest sensitivity could be attained.

Example 5

Comparison of Substrate Degradation Rate in Relation to Difference in Substrate Form for apr Rnase H Degradation rates of RNase H were determined using one of three DNA-RNA-DNAs containing different numbers of RNAs in their sequences (probeW1 (SEQ ID NO:13), probeW2 (SEQ ID NO:14) and probeW3 (SEQ ID NO:15)) as a substrate, and the differences were examined. In addition, cleavage rates of RNase HII from *Pyrococcus furiosus* (Pfu RNase HII) and RNase HII from *Pyrococcus horikoshii* (Pho RNase HII) prepared as described in WO 02/22831 as well as RNase HI from *Thermus thermophilus* (Tth RNase HI) (Toyobo) using the above-mentioned substrates were compared.

If a solution containing probeW1, probeW2 or probeW3 is exposed to light at wavelength around the maximum excitation wavelength of FAM (495 nm), FAM as a modification at the 5' end of the substrate emits fluorescence at the maximum wavelength 519 nm. However, the fluorescence is attenuated as a result of fluorescence resonance energy transfer (FRET) with DABCYL as a modification at the 3' end. If the substrate is cleaved with RNase H, the intensity of fluorescence at 519 nm is increased as a result of relief of FRET. Thus, degradation of the substrate can be monitored by determining the difference between intensities of fluorescence at 519 nm measured before and after cleavage of the substrate.

If substrate concentration is sufficiently high as compared with enzyme concentration, the amount of enzymatic reaction product is increased in proportion to time. If a degradation rate is to be monitored by determining fluorescence intensity at 519 nm using a substrate in an amount sufficiently excessive as compared with the amount of enzyme, increase in fluorescence intensity per unit time at the beginning of a reaction can be approximated using a linear equation. The slope of the approximation line corresponds to increase in fluorescence intensity per time ((fluorescence intensity)/(minute)). Assuming that a substrate in a reaction system is completely degraded when increase in fluorescence intensity reaches a plateau and the fluorescence intensity reaches its maximum value, (maximum fluorescence intensity)−(fluorescence intensity before cleavage) corresponds to increase in fluorescence intensity per amount of degraded substrate. Reaction rate v ((amount of degraded substrate)/(minute)) can be determined based on this value and the increase in fluorescence intensity per time ((fluorescence intensity)/(minute)).

Apr RNase H at a final concentration of 0.4, 0.8, 1.6 or 2.4 unit(s)/ml was added to an activity measurement solution (at final concentrations, 32 mM HEPES-potassium hydroxide buffer (pH 7.8), 100 mM potassium acetate, 1% DMSO, 0.05% BSA, 4 mM magnesium acetate, 0.2 µM substrate DNA-RNA-DNA and 1 µM templateW49 (SEQ ID NO:16)). A real-time PCR measurement instrument Smart Cycler (Takara Bio) was used for RNase H reaction and fluorescence intensity measurement. Reaction rate v ((amount of degraded substrate)/(minute)) was determined by conducting a reaction at 55° C. for 100 minutes. Reaction rate per enzyme unit ((amount of degraded substrate)/(minute·unit)) was determined based on a slope of a calibration curve prepared by plotting reaction rate v ((amount of degraded substrate)/(minute)) against Apr RNase H concentration. Activity measurements were carried out using Pfu RNase HII, Pho RNase HII or Tth RNase HI in a similar manner to determine reaction rates per enzyme unit ((amount of degraded substrate)/(minute·unit)). In case of Tth RNase HI, Tth RNase HI was added to the activity measurement solution at a final concentration of 10, 20, 30 or 40 units/ml.

Reaction rates per enzyme unit of the respective enzymes determined using probeW1, probeW2 or probeW3 are shown in Table 2. Values in pmol/(minute·unit) are shown in the table. Relative reaction rates defining reaction rate per enzyme unit using probeW3 as 100% are indicated in parentheses. Using Apr RNase H, cleavage rates higher than those observed using other RNase Hs were observed in all cases of various RNA numbers. The highest cleavage rate was observed using the substrate having two RNAs. The cleavage rates observed using the substrates having one or two RNA(s) were close to the cleavage rate observed using the substrate having three RNAs.

TABLE 2

|  | probeW1 (RNA = 1) | probeW2 (RNA = 2) | probeW3 (RNA = 3) |
| --- | --- | --- | --- |
| Apr RNase HII | 17.0 (61.6) | 41.1 (148.9) | 27.6 (100) |
| Pfu RNase HII | 3.3 (34.8) | 5.3 (55.9) | 9.5 (100) |
| Pho RNase HII | 2.7 (55.6) | 3.2 (67.8) | 4.8 (100) |
| Tth RNase HI | 0.0 (0) | 0.0 (2.2) | 1.4 (100) |

As described above, it was shown that Apr RNase H whose cleavage rate is less susceptible to influence of RNA length is useful for nucleic acid amplification reactions and nucleic acid detection reactions.

INDUSTRIAL APPLICABILITY

The present invention provides a polypeptide having an RNase H activity which is highly valuable for genetic engineering, a gene encoding said polypeptide and a method for producing said polypeptide by genetic engineering. Since the RNase H of the present invention is thermostable, the present invention provides a method for producing an RNase H which is industrially advantageous.

It is now possible to use the RNase H of the present invention for various uses according to the present invention.

Sequence Listing Free Text

SEQ ID NO:3: PCR primer RN-F1 for cloning a gene encoding a polypeptide having a RNaseH activity from *Archaeoglobus profundus*

SEQ ID NO:4: PCR primer RN-R2 for cloning a gene encoding a polypeptide having a RNaseH activity from *Archaeoglobus profundus*

SEQ ID NO:5: PCR primer AprRN-1 for cloning a gene encoding a polypeptide having a RNaseH activity from *Archaeoglobus profundus*

SEQ ID NO:6: PCR primer AprRN-2 for cloning a gene encoding a polypeptide having a RNaseH activity from *Archaeoglobus profundus*

SEQ ID NO:7: Tag sequence

SEQ ID NO:8: PCR primer AprNde for amplifying a gene encoding a polypeptide having a RNaseH activity from *Archaeoglobus profundus*

SEQ ID NO:9: PCR primer AprBam for amplifying a gene encoding a polypeptide having a RNaseHII activity from *Archaeoglobus profundus*

SEQ ID NO:11: Chimeric oligonucleotide primer to amplify a portion of Hepatitis B virus X protein. "nucleotides 18 to 20 are ribonucleotides—other nucleotides are deoxyribonucleotides"

SEQ ID NO:12: Chimeric oligonucleotide primer to amplify a portion of Hepatitis B virus X protein. "nucleotides 20 to 22 are ribonucleotides—other nucleotides are deoxyribonucleotides"

SEQ ID NO:13: Chimeric oligonucleotide designed as probeW1. "nucleotide 9 is ribonucleotides—other nucleotides are deoxyribonucleotides"

SEQ ID NO:14: Chimeric oligonucleotide designed as probeW2. "nucleotides 9 to 10 are ribonucleotides—other nucleotides are deoxyribonucleotides"

SEQ ID NO:15: Chimeric oligonucleotide designed as probeW3. "nucleotides 9 to 11 are ribonucleotides—other nucleotides are deoxyribonucleotides"

SEQ ID NO:16: Oligonucleotide designed as templateW49.

The invention claimed is:

1. An isolated polypeptide having a thermostable ribonuclease H activity, and having the amino acid sequence of SEQ ID NO:1.

2. An isolated polypeptide having a thermostable ribonuclease H activity encoded by plasmid pApr108, and wherein said polypeptide is obtained by culturing a transformant into which plasmid pApr108 harbored by *Escherichia coli* HMS174/pApr108 (deposited under accession no. FERM BP-8433) is transferred.

* * * * *

SEQUENCE LISTING

<160> NUMBER OF SEQ ID NOS: 16

<210> SEQ ID NO 1
<211> LENGTH: 211
<212> TYPE: PRT
<213> ORGANISM: Archaeoglobus profundus

<400> SEQUENCE: 1

Met Ile Ala Gly Ile Asp Glu Ala Gly Lys Gly Pro Val Ile Gly Pro
1               5                   10                  15

Leu Val Ile Cys Gly Val Leu Cys Asp Glu Glu Thr Val Glu Tyr Leu
            20                  25                  30

Lys Ser Val Gly Val Lys Asp Ser Lys Lys Leu Asp Arg Arg Lys Arg
        35                  40                  45

Glu Glu Leu Tyr Asn Ile Ile Lys Ser Leu Cys Lys Val Lys Val Leu
    50                  55                  60

Lys Ile Ser Val Glu Asp Leu Asn Arg Leu Met Glu Tyr Met Ser Ile
65                  70                  75                  80

Asn Glu Ile Leu Lys Arg Ala Tyr Val Glu Ile Ile Arg Ser Leu Met
                85                  90                  95

Pro Lys Val Val Tyr Ile Asp Cys Pro Asp Ile Asn Val Glu Arg Phe
            100                 105                 110

-continued

```
Lys His Glu Ile Glu Arg Thr Gly Val Glu Val Phe Ala Ser His
            115                 120                 125

Lys Ala Asp Glu Ile Tyr Pro Ile Val Ser Ile Ala Ser Ile Val Ala
130                 135                 140

Lys Val Glu Arg Asp Phe Glu Ile Asp Lys Leu Lys Lys Ile Tyr Gly
145                 150                 155                 160

Asp Phe Gly Ser Gly Tyr Pro Ser Asp Leu Arg Thr Ile Glu Phe Leu
                165                 170                 175

Arg Ser Tyr Leu Arg Glu His Lys Ser Phe Pro Pro Ile Val Arg Lys
            180                 185                 190

Arg Trp Lys Thr Leu Lys Arg Leu Thr Thr His Thr Leu Ser Asp Phe
        195                 200                 205

Phe Glu Val
    210

<210> SEQ ID NO 2
<211> LENGTH: 636
<212> TYPE: PRT
<213> ORGANISM: Archaeoglobus profundus

<400> SEQUENCE: 2

Ala Thr Gly Ala Thr Thr Gly Cys Thr Gly Gly Ala Thr Ala Gly
1               5                   10                  15

Ala Cys Gly Ala Ala Gly Cys Thr Gly Gly Ala Ala Ala Gly Gly
            20                  25                  30

Ala Cys Cys Thr Gly Thr Ala Ala Thr Ala Gly Gly Cys Cys Thr
            35                  40                  45

Cys Thr Thr Gly Thr Ala Ala Thr Ala Thr Gly Cys Gly Gly Ala Gly
    50                  55                  60

Thr Ala Cys Thr Gly Thr Gly Cys Gly Ala Thr Gly Ala Ala Gly Ala
65                  70                  75                  80

Gly Ala Cys Cys Gly Thr Ala Gly Ala Ala Thr Ala Cys Thr Thr Gly
                85                  90                  95

Ala Ala Gly Ala Gly Cys Gly Thr Ala Gly Gly Cys Gly Thr Thr Ala
            100                 105                 110

Ala Ala Gly Ala Thr Thr Cys Ala Ala Ala Gly Ala Ala Gly Cys Thr
            115                 120                 125

Gly Gly Ala Thr Ala Gly Gly Ala Gly Gly Ala Ala Gly Ala Gly Ala
    130                 135                 140

Gly Ala Gly Gly Ala Ala Cys Thr Thr Ala Cys Ala Ala Thr Ala
145                 150                 155                 160

Thr Cys Ala Thr Ala Ala Ala Ala Thr Cys Gly Cys Thr Thr Thr Gly
                165                 170                 175

Cys Ala Ala Gly Gly Thr Thr Ala Ala Gly Gly Thr Ala Thr Thr Gly
            180                 185                 190

Ala Ala Ala Ala Thr Ala Cys Thr Gly Thr Cys Gly Ala Gly Gly
            195                 200                 205

Ala Thr Thr Gly Ala Ala Cys Ala Gly Gly Thr Ala Thr Ala Ala Thr
    210                 215                 220

Gly Gly Ala Ala Thr Ala Cys Ala Thr Gly Ala Gly Thr Ala Thr Ala
225                 230                 235                 240

Ala Ala Thr Gly Ala Ala Ala Thr Cys Thr Thr Gly Ala Ala Gly Ala
                245                 250                 255

Gly Ala Gly Cys Thr Thr Ala Cys Gly Thr Thr Gly Ala Ala Ala Thr
```

```
                260                 265                 270
Ala Ala Thr Ala Ala Gly Gly Thr Cys Thr Thr Thr Gly Ala Thr Gly
            275                 280                 285
Cys Cys Thr Ala Ala Gly Thr Thr Thr Gly Thr Ala Cys Ala
        290                 295                 300
Thr Ala Gly Ala Cys Thr Gly Thr Cys Ala Gly Ala Thr Ala Thr
305                 310                 315                 320
Thr Ala Ala Thr Gly Thr Gly Gly Ala Gly Ala Thr Thr Thr
            325                 330                 335
Ala Ala Gly Cys Ala Cys Gly Ala Ala Ala Thr Ala Gly Ala Gly Gly
        340                 345                 350
Ala Gly Ala Gly Ala Ala Cys Gly Gly Ala Gly Thr Gly Gly Ala
            355                 360                 365
Gly Gly Thr Ala Thr Thr Thr Gly Cys Gly Ala Gly Cys Cys Ala Thr
        370                 375                 380
Ala Ala Ala Gly Cys Gly Gly Ala Cys Gly Gly Ala Thr Ala Thr
385                 390                 395                 400
Ala Thr Cys Cys Ala Ala Thr Ala Gly Thr Ala Thr Cys Thr Ala Thr
            405                 410                 415
Ala Gly Cys Thr Thr Cys Gly Ala Thr Ala Gly Thr Cys Gly Cys Ala
        420                 425                 430
Ala Ala Ala Gly Thr Thr Gly Ala Ala Ala Gly Gly Gly Ala Thr Thr
            435                 440                 445
Thr Thr Gly Ala Ala Ala Thr Ala Gly Ala Cys Ala Ala Gly Cys Thr
        450                 455                 460
Gly Ala Ala Gly Ala Ala Gly Ala Thr Thr Thr Ala Thr Gly Gly Ala
465                 470                 475                 480
Gly Ala Cys Thr Thr Thr Gly Gly Gly Ala Gly Thr Gly Gly Ala Thr
            485                 490                 495
Ala Thr Cys Cys Ala Thr Cys Ala Gly Ala Thr Cys Thr Ala Ala Gly
        500                 505                 510
Ala Ala Cys Cys Ala Thr Cys Gly Ala Ala Thr Thr Thr Thr Ala
            515                 520                 525
Ala Gly Gly Ala Gly Thr Thr Ala Thr Cys Thr Ala Ala Gly Gly Gly
        530                 535                 540
Ala Ala Cys Ala Cys Ala Ala Ala Gly Thr Thr Thr Cys Cys
545                 550                 555                 560
Ala Cys Cys Ala Ala Thr Cys Gly Thr Ala Ala Gly Ala Ala Ala Gly
            565                 570                 575
Ala Gly Ala Thr Gly Gly Ala Ala Ala Ala Cys Thr Cys Thr Cys Ala
        580                 585                 590
Ala Ala Ala Gly Ala Thr Thr Gly Ala Cys Ala Ala Cys Gly Cys Ala
            595                 600                 605
Cys Ala Cys Thr Thr Thr Ala Ala Gly Cys Gly Ala Thr Thr Thr Cys
        610                 615                 620
Thr Thr Thr Gly Ala Ala Gly Thr Thr Ala Gly
625                 630                 635
```

<210> SEQ ID NO 3
<211> LENGTH: 23
<212> TYPE: DNA
<213> ORGANISM: Artificial
<220> FEATURE:
<223> OTHER INFORMATION: synthetic
<220> FEATURE:

<221> NAME/KEY: misc_feature
<223> OTHER INFORMATION: PCR primer RN-F1 for cloning a gene encoding a
      polypeptide having a RNaseH activity from Archaeoglobus profundus
<220> FEATURE:
<221> NAME/KEY: misc_feature
<222> LOCATION: (18)..(18)
<223> OTHER INFORMATION: n is a, c, g, or t

<400> SEQUENCE: 3
ggcattgatg aggctggnar rgg                                           23

<210> SEQ ID NO 4
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer RN-R2 for cloning a gene encoding a
      polypeptide having a RNaseH activity from Archaeoglobus profundus
<220> FEATURE:
<221> NAME/KEY: misc_feature
<222> LOCATION: (18)..(18)
<223> OTHER INFORMATION: n is a, c, g, or t

<400> SEQUENCE: 4
ggtagggaaa gctgraancg                                               20

<210> SEQ ID NO 5
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer AprRN-1 for cloning a gene encoding
      a polypeptide having a RNaseH activity from Archaeoglobus
      profundus

<400> SEQUENCE: 5
ctcttcatcg cacagtactc cg                                            22

<210> SEQ ID NO 6
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer AprRN-2 for cloning a gene encoding
      a polypeptide having a RNaseH activity from Archaeoglobus
      profundus

<400> SEQUENCE: 6
tttgcgagcc ataaagcgga cg                                            22

<210> SEQ ID NO 7
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Tag sequence

<400> SEQUENCE: 7

```
ggcacgattc gataacg                                                       17
```

<210> SEQ ID NO 8
<211> LENGTH: 39
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer AprNde for amplifying a gene
      encoding a polypeptide having a RNaseH activity from
      Archaeoglobus profundus

<400> SEQUENCE: 8

```
aatcgatggt gttcatatga ttgctgggat agacgaagc                               39
```

<210> SEQ ID NO 9
<211> LENGTH: 39
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer AprBam for amplifying a gene
      encoding a polypeptide having a RNaseHIII activity from
      Archaeoglobus profundus

<400> SEQUENCE: 9

```
gcccacgccc tgggatccct aggctacggg tcctttaag                               39
```

<210> SEQ ID NO 10
<211> LENGTH: 560
<212> TYPE: DNA
<213> ORGANISM: Hepatitis B virus

<400> SEQUENCE: 10

```
ccttcccatg gctgctcggg tgtgctgcca actggatcct gcgcgggacg tcctttgtct        60
acgtcccgtc ggcgctgaat cccgcggacg accgtctcg  gggccgtttg ggcctctacc       120
gtcccttgct ttctctgccg ttccagccga ccacggggcg cacctctctt tacgcggtct       180
ccccgtctgt gccttctcat ctgccggacc gtgtgcactt cgcttcacct ctgcacgtcg       240
catggagacc accgtgaacg ccaccaggt  cttgcccaag ctcttacata agaggactct       300
tggactctca gcaatgtcaa caaccgacct tgaggcatac ttcaaagact gtttgtttaa       360
agactgggag gagttggggg aggagattag gttaaaggtc tttgtactag gaggctgtag       420
gcataaattg gtctgttcac cagcaccatg caacttttc  acctctgcct aatcatctca       480
tgttcatgtc ctactgttca agcctccaag ctgtgccttg ggtggctttg ggcatggac        540
attgacccgt ataaagaatt                                                  560
```

<210> SEQ ID NO 11
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide primer to amplify a
      portion of Hepatitis B virus X protein.
<220> FEATURE:
<221> NAME/KEY: misc_feature
<222> LOCATION: (18)..(20)
<223> OTHER INFORMATION: nucleotides 18 to 20 are ribonucleotides-other nucleotides are deoxyribonucleotides

<400> SEQUENCE: 11
ctcttggact ctcagcaaug                                              20

<210> SEQ ID NO 12
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide primer to amplify a
      portion of Hepatitis B virus X protein.
<220> FEATURE:
<221> NAME/KEY: misc_feature
<222> LOCATION: (20)..(22)
<223> OTHER INFORMATION: nucleotides 20 to 22 are ribonucleotides-other
      nucleotides are deoxyribonucleotides

<400> SEQUENCE: 12
tcctcccagt ctttaaacam ac                                           22

<210> SEQ ID NO 13
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide designed as probeW1.
<220> FEATURE:
<221> NAME/KEY: misc_feature
<222> LOCATION: (9)..(9)
<223> OTHER INFORMATION: nucleotide 9 is ribonucleotides-other
      nucleotides are deoxyribonucleotides

<400> SEQUENCE: 13
cctacgccac cagctccaac                                              20

<210> SEQ ID NO 14
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide designed as probeW2.
      nucleotides
<220> FEATURE:
<221> NAME/KEY: misc_feature
<222> LOCATION: (9)..(10)
<223> OTHER INFORMATION: nucleotides 9 to 10 are ribonucleotides-other
      nucleotides are deoxyribonucleotides

<400> SEQUENCE: 14
cctacgccac cagctccaac                                              20

<210> SEQ ID NO 15
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide designed as probeW3.
<220> FEATURE:

```
<221> NAME/KEY: misc_feature
<222> LOCATION: (9)..(11)
<223> OTHER INFORMATION: nucleotides 9 to 11 are ribonucleotides-other
      nucleotides are deoxyribonucleotides

<400> SEQUENCE: 15
cctacgccac cagctccaac                                                    20

<210> SEQ ID NO 16
<211> LENGTH: 49
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Oligonucleotide designed as templateW49.

<400> SEQUENCE: 16
ataaacttgt ggtagttgga gctggtggcg taggcaagag tgccttgac                    49
```